US008314058B2

(12) United States Patent
New (10) Patent No.: US 8,314,058 B2
(45) Date of Patent: *Nov. 20, 2012

(54) UPTAKE OF MACROMOLECULES

(75) Inventor: Roger R. C. New, London (GB)

(73) Assignee: Axcess Limited, St. Helier (JE)

( * ) Notice: Subject to any disclaimer, the term of this patent is extended or adjusted under 35 U.S.C. 154(b) by 0 days.

This patent is subject to a terminal disclaimer.

(21) Appl. No.: 10/553,169

(22) PCT Filed: Apr. 15, 2004

(86) PCT No.: PCT/GB2004/001651

§ 371 (c)(1),
(2), (4) Date: Nov. 28, 2005

(87) PCT Pub. No.: WO2004/091667

PCT Pub. Date: Oct. 28, 2004

(65) Prior Publication Data

US 2006/0122097 A1 Jun. 8, 2006

(30) Foreign Application Priority Data

Apr. 15, 2003 (GB) .................................. 0308734.3

(51) Int. Cl.
*A61K 38/02* (2006.01)
*A61K 38/22* (2006.01)
*A61K 38/23* (2006.01)
*A61K 38/26* (2006.01)
*A61K 38/27* (2006.01)
*A61K 38/28* (2006.01)
*A61K 38/36* (2006.01)

(52) U.S. Cl. ............ 514/1.1; 514/6.7; 514/7.2; 514/7.7; 514/11.3; 514/11.9

(58) Field of Classification Search ........................ None
See application file for complete search history.

(56) References Cited

U.S. PATENT DOCUMENTS

| 3,996,355 | A | | 12/1976 | Lin et al. | |
| 4,789,660 | A | | 12/1988 | Enever et al. | |
| 5,206,219 | A | * | 4/1993 | Desai ................................. | 514/3 |
| 5,342,625 | A | | 8/1994 | Hauer et al. | |
| 5,645,856 | A | * | 7/1997 | Lacy et al. ...................... | 424/455 |
| 5,653,987 | A | * | 8/1997 | Modi et al. ...................... | 424/400 |
| 5,756,450 | A | | 5/1998 | Hahn et al. | |
| 5,849,700 | A | | 12/1998 | Sorensen et al. | |
| 5,849,704 | A | | 12/1998 | Sorensen et al. | |
| 5,853,748 | A | * | 12/1998 | New .............................. | 424/439 |
| 5,891,671 | A | | 4/1999 | Suzuki et al. | |
| 5,962,522 | A | | 10/1999 | Wacher et al. | |
| 6,180,666 | B1 | | 1/2001 | Wacher et al. | |
| 6,342,249 | B1 | | 1/2002 | Wong et al. | |
| 6,358,924 | B1 | | 3/2002 | Hoffmann | |
| 7,446,091 | B2 | | 11/2008 | Van Den Berghe | |
| 7,491,187 | B2 | | 2/2009 | Van Den Berghe et al. | |
| 2001/0014675 | A1 | | 8/2001 | Loria | |
| 2003/0069170 | A1 | * | 4/2003 | Soltero et al. .................. | 514/2 |
| 2003/0232078 | A1 | | 12/2003 | Dong | |
| 2006/0122097 | A1 | | 6/2006 | New et al. | |
| 2006/0223740 | A1 | | 10/2006 | New | |

FOREIGN PATENT DOCUMENTS

| EP | 0 127 535 | | 12/1984 |
| EP | 0 295 941 | | 12/1988 |
| EP | 0 371 010 | A1 | 5/1990 |
| EP | 0 591 432 | B1 | 9/2002 |
| GB | 354184 | | 7/1931 |
| JP | 52-057313 | A | 11/1975 |
| JP | 56-138168 | | 10/1981 |
| JP | 56138168 | A * | 10/1981 |
| JP | 5-246846 | | 9/1993 |
| JP | 11-507356 | | 6/1999 |
| JP | 11-508606 | | 7/1999 |
| JP | 2001-514234 | | 9/2001 |
| JP | 2002-538173 | | 11/2002 |
| JP | 2005-508938 | | 4/2005 |
| WO | 93/06854 | | 4/1993 |
| WO | 96/40192 | | 12/1996 |
| WO | WO 96/40192 | | 12/1996 |
| WO | 97/21448 | | 6/1997 |
| WO | 97/33531 | | 9/1997 |
| WO | WO 97/33531 | | 9/1997 |
| WO | WO 98/00169 | | 1/1998 |
| WO | WO 99/11290 | | 3/1999 |
| WO | WO 99/29336 | | 6/1999 |
| WO | WO 00/22909 | * | 4/2000 |
| WO | WO 00/51643 | | 8/2000 |
| WO | 2000-515130 | | 11/2000 |
| WO | WO 01/74169 | A1 | 10/2001 |
| WO | WO 02/22158 | | 3/2002 |
| WO | WO 02/28436 | | 4/2002 |
| WO | WO 03/022208 | A2 | 3/2003 |
| WO | WO 03/030865 | | 4/2003 |

OTHER PUBLICATIONS

Bradley, C. "The glitazones: a new treatment for type 2 diabetes melitus." Int. Crit. Care Nurs. 2002, 18, 189-91.*
Strickley, R.G., Anderson, B.D. "Solid-State Stability of Human Insulin II. Effect of Water on Reactive Intermediate Partitioning in Lyophiles from pH 2-5 Solutions: Stabilization against Covalent Dimer Formation." J. Pharm. Sci. 1997, 86 (6), 645-53.*
Harsch et al. "Syringe, pen, inhaler—the evolution of insulin therapy." Med. Sci. Monit. 2001, 7(4), 833-836.*
Liu et al. "Cancer gene therapy targeting angiogenesis: An updated review." World J. Gastroenterol., 2006, 12, 6941-8.*
Sutter et al. "Gene therapy for gastric cancer: is it promising?" World J Gastroenterol., 2006, 12, 380-7.*
"Dissociation Constants of Organic Acids and Bases," CRC Handbook of Chemistry and Physics, $83^{rd}$ edition, 2002, p. 8-49.*
Ivanovic et al., "Effect of pH on the Retention Behaviorof Some Preservatives-Antioxidants in Reversed-Phase High-Performance Liquid Chromatography," Chromatographia, 1995, 40, 652-6.*
Sonnenberg & Kotchen, "New therapeutic approaches to reversing insulin resistance," Curr. Op. Neph. Hyperten., 1998, 7, 551-5.*
Alberts et al. Molecular Biology of the Cell, 4th ed., chapter 22, http://www.ncbi.nlm.nih.gov/books/bv.
fcgi?highlight=small%20intestine,pH&rid=mboc4.section.
4113#4118, pp. 1-6.*

(Continued)

*Primary Examiner* — Julie Ha
(74) *Attorney, Agent, or Firm* — Nixon & Vanderhye P.C.

(57) ABSTRACT

The invention provides a pharmaceutical composition comprising a mixture of: (a) an active macromolecular principle; and (b) a non-conjugated bile acid or salt; and (c) an additive chosen from propyl gallate, butyl hydroxy anisole (BHA) and analogues and derivatives thereof, or mixtures thereof.

32 Claims, 3 Drawing Sheets

OTHER PUBLICATIONS

GenBnak Accession No. CAA26189 for Calcitonin. Accessed Jul. 30, 2008.*
GenBnak Accession No. AAA49464 for growth hormone. Accessed Jul. 30, 2008.*
Growth Hormone from GenBank Accession No. NP-001075417, pp. 1-2. Accessed Jan. 29, 2009.*
Growth Hormone from GenBank Accession No. CAA54461, pp. 1-2. Accessed Jan. 29, 2009.*
Parathyroid Hormone from GenBank Accession No. AAA72730, pp. 1-2. Accessed Jan. 29, 2009.*
International Search Report of PCT/GB2004/001651, mailed Aug. 30, 2004.
Database WPI, Section Ch, Week 198149, Derwent Publications Ltd., AN 1981-90325D, XP002292155.
Shen et al, "Pulmonary Delivery of Insulin: Absorption Enhancement of Insulin by Various Absorption Promoters in Rats", Journal of Chinese Pharmaceutical Sciences (2000), 9(1), 22-25.
Sigma "Product Information" extract for insulin, pp . 1-3, Oct. 7, 1996.
Brange et al, "Chemical stability of insulin", Acta Pharm. Nord. 4(3); 149-158 (1992).
A US EPA report entitled "Alkylphenois Category (Section One)", pp . 1-41, Apr. 19, 2006 stamped.
Hidalgo et al, "Characterization of the Human Colon Carcinoma Cell Line (Caco-2) as a Model System . . . ", Gastroenterology 1989; 96:736-49.
Hilgers et al, "Caco-2 Cell Monolayers as a Model for Drug Transport Across the Intestinal Mucosa", Pharmaceutical Research, vol. 7, No. 9, 1990.
Sambuy et al, "The Caco-2 cell line as a model of the intestinal barrier: influence of cell and culture-related factors on Caco-2 cell functional characteristics", Cell Biology and Toxicology, 2005; 21: 1-26.
He et al, "Absorption of Ester Prodrugs in Caco-2 and Rat Intestine Models", Antimicrobial Agents and Chemotherapy, Jul. 2004, p. 2604-2609, vol. 48, No. 7.
Grasset et al, "Epithelial properties of human colonic carcinoma cell line Caco-2: electrical parameters", American Journal of Physiology, 1984, C260-C267.
Hirakata et al, "Adherence to and Penetration of Human Intestinal Caco-2 Epithelial Cell Monolayers of *Pseudomonas aeruginosa*", Infection and Immunity, Apr. 1998, pp. 1748-1751; vol. 66, No. 4.
STN Registry of Nov. 16, 1984.
Extract from the Thirteenth Edition of the Merck Index for Pioglitazone; 2001, p. 1335.
Database of Select Committee on GRAS Substances (SCOGS) Reviews— Propyl Gallate, 1973.
Database of Select Committee on GRAS Substances (SCOGS) Reviews—Butylated Hydroxytoluene (BHT), 1973.
Database of Select Committee on GRAS Substances (SCOGS) Reviews—Butylated Hydroxyanisole (BHA), 1978.
Handbook of Pharmaceutical Excipients, Second Edition, Edited by Ainley Wade and Paul J. Weller, 1994, "Propyl Gallate", pp. 402, 403, 404.
Handbook of Pharmaceutical Excipients, Second Edition, Edited by Ainley Wade and Paul J. Weller, 1994, "Butylated Hydroxytoluene", pp. 47, 48.
Handbook of Pharmaceutical Excipients, Second Edition, Edited by Ainley Wade and Paul J. Weller, 1994, "Butylated Hydroxyanisole", pp. 45, 46.
International Search Report of PCT/GB2004/001650, mailed Sep. 28, 2004.
Van Hoogdalem et al., "Intestinal Drug Absorption Enhancement: An Overview", Pharmacology and Therapeutics, Elsevier, vol. 44, No. 3, 1989, pp. 407-443, XP002086283.
Aungst et al., "Enhancement of the Intestinal Absorption of Peptides and Non-peptides", Journal of Controlled Release, vol. 41, No. 1-2, 1996, pp. 19-31, XP004037568.
Dondeti et al., "In Vivo Evaluation of Spray Formulations of Human Insulin for Nasal Delivery", International Journal of Pharaceutics, vol. 122, No. 1-2, 1995, pp. 91-105, XP002295623.
Sasaki et al., "Effect of Ophtalmic Preservatives on Serum Concentration and Local Irritation of Ocularly Applied Insulin", Biological and Pharmaceutical Bulletin, vol. 18, No. 1, 1995, pp. 169-171, XP001183131.
Read et al, Antisense Strategies . . . , 2002, Expert Opinion. Ther. Patents, vol. 12, pp. 379-391.
Dressman et al, "In vitro-in vivo correlations for lipophilic, poorly water-soluble drugs", European Journal of Pharmaceutical Sciences 11 Suppl. 2(2000) S73-S80.
Handbook of Pharmaceutical Excipients, Eds Wade & Weller, The Pharmaceutical Press, London UK $2^{nd}$ Edition, 1994.
Chang et al, "Effect of a lipoidic excipient on the absorption profile . . . ", J. Pharm. Pharmaceut. Sci (www.ualberta.ca/—csps) &(1):8-12, 2004.
Atta et al, "Influence of a Niosomal Formulation on the Oral Bioavailability . . . ", AAPS PharmSciTech 2007; 8(4) Article 106 (http://www.aapspharmscitech.org).
Ke et al, "Enhanced Oral Bioavailability of Doxorubicin in a Dendrimer . . . ", Journal of Pharmaceutical Sciences, vol. 97, No. 6, Jun. 2008.
Extract from the Merck index (p. 480 and title page), 2001.
A US EPA report entitled "Alkylphenois Category (Section One)" , pp. 1-41, 2006.

* cited by examiner

UPTAKE OF MACROMOLECULES

This application is the US national phase of international application PCT/GB2004/001651, filed 15 Apr. 2004, which designated the U.S. and claims priority of GB 0308734.3, filed 15 Apr. 2003, the entire contents of each of which are hereby incorporated by reference.

This invention relates to a pharmaceutical composition and the use of materials having efficacy in enhancement of uptake of macromolecules from the lumen of the intestine across the gut wall and into the rest of the body in the preparation of a medicament. In particular, formulations are described in which bile salts are combined with other materials in such a way as to improve the performance of these bile salts (in terms of efficacy, reproducibility, or stability) compared with formulations employed to date.

Bile salts are already recognised as highly effective permeation enhancers in the intestine. They are surface-active compounds that can incorporate readily into phospholipid membranes of cells and bring about a number of changes in cell behaviour and morphology. While the precise mechanism of action is unknown, one possible mode of action is the transient opening of tight junctions in between enterocytes, allowing materials in the vicinity to pass in between these cells and into the extracellular fluid basal to the enterocyte layer. Evidence for this is provided by experiments from laboratories demonstrating reduction in trans epithelial electrical resistance (TEER) of enterocyte cell monolayers, indicative of the formation of aqueous channels in between cells, capable of conducting electricity unimpeded.

Since peristaltic action in the intestine tends to encourage rapid dispersion of pharmaceutical formulations over a larger surface area, it is important that the bile salts in the formulation should dissolve rapidly, and remain in the form of a solution for a long as possible, so that the local concentration of bile salt may be maintained as high as possible in order for it to exert its maximal effect. For this reason, most workers have employed conjugated bile salts such as taurocholate or taurodeoxycholate, since these are readily soluble over a wide range of pH, including pH values as low as 3, which may be found in the intestine. These bile salts, however, are not as efficacious as some non-conjugated, particularly deoxy bile salts, such as chenodeoxycholate or deoxycholate, although these are often not soluble at pH values much below neutrality. Thus the performance of non-conjugated bile salts as a permeation enhancer would be expected to be very variable, depending upon the pH in the area of the intestine where it was operating, which in turn would determine whether the bile salt was present as a solution (efficacious) or a precipitate (poorly efficacious).

In order to overcome this lack of reproducibility, approaches have been described in which the bile salt is combined with an agent which adjusts the pH in the gut to greater than 7.5, in order to ensure that the bile salt is in soluble form. Unfortunately, the inclusion of such agents in the formulation can adversely affect the integrity and stability of sensitive actives included in the formulation such as peptides and proteins. Also, the pH optimum for intestinal proteases is known to be around pH 8, so that the adoption of such an approach may increase degradation due to endogenous protease activity.

The present invention describes an alternative approach in which bile salts are combined with additives that, surprisingly, are able to maintain these bile salts in solution at pH values below 7, equivalent to those pH values commonly encountered in the small intestine. In particular, it has been found that co-formulation of bile salts either with propyl gallate or derivatives, or with salts of organic acids, can give rise to solid powders which, when added to simulated intestinal fluids in a wide range of different proportions, are readily dissolved, even when the initial pH of the fluid is as low as pH5. Suitable simulated intestinal fluids which may be used as models for the lumenal contents of the intestine in either fed or fasted states are described by Dressman and coworkers (Dressman, B Jennifer & Reppas, Christos. *European Journal of Pharmaceutical Sciences* 11 Suppl 2 (2000) S73-S80 "In vitro-in vivo correlations for lipophilic, poorly water-soluble drugs.").

The compositions described in this invention are particularly advantageous when preparing solid-dose formulations for oral administration either as enteric-coated capsules or tablets. The solid components of the composition may also be incorporated into a pharmaceutical formulation as a dispersion in a non-aqueous liquid.

In the case of propyl gallate, which is a very water-insoluble material, it has been found, surprisingly, that co-formulation with bile salts, including chenodeoxycholate, can markedly enhance the solubilisation of propyl gallate in water, and particularly in simulated intestinal fluids. Thus, chenodeoxycholate and propyl gallate are able mutually to enhance each other's aqueous solubility at pH levels below pH 7. In view of the fact that propyl gallate itself is highly water-insoluble, it would not be anticipated that addition to chenodeoxycholate would result in a formulation which was more readily soluble, and a person skilled in the art would not be motivated to attempt such a procedure.

The invention provides a pharmaceutical composition comprising a mixture of:
 (a) an active macromolecular principle; and
 (b) a non-conjugated bile acid or salt; and
 (c) an additive chosen from propyl gallate and butyl hydroxy anisole and analogues and derivatives thereof, or mixtures thereof.

The invention also provides the use, in a pharmaceutical composition, of a non-conjugated bile acid or salt, together with an additive chosen from propyl gallate and BHA and analogues and derivatives thereof, or mixtures thereof as an enhancer for the absorption of macromolecules across the intestinal wall.

In a further embodiment the invention provides the use of a non-conjugated bile acid or salt, together with an additive chosen from propyl gallate and BHA and analogues and derivatives thereof, or mixtures thereof in the manufacture of a medicament containing an active macromolecular principle, in order to enhance absorption of the active macromolecular principle into the human or animal body.

The active macromolecular principles falling within the scope of the invention include all molecules capable of having a beneficial effect when absorbed into the human or animal body, especially through the intestinal wall. The beneficial effect may be, for example, therapeutic, cosmetic or preventative such as prophylactic or contraceptive. The active macromolecular principles can be of natural (biological), synthetic or semi-synthetic origin.

Macromolecules are preferably defined as molecules having a molecular weight of over 1000 Da, preferably over 2000 Da and most preferably over 3000 Da. Examples of macromolecules, including macromolecular active macromolecular principles, include:

1. Polypeptides and proteins such as insulin; calcitonin; human serum albumin; growth hormone; growth hormone releasing factors; galanin; parathyroid hormone; blood clotting proteins such as kinogen, prothrombin, fibrinogen, Factor VII, Factor VIII of Factor IX; erythropoeitins and EPO mimetics; colony stimulating factors including GCSF and GMCSF; platelet-derived growth factors; epidermal growth factors; fibroblast growth factors; transforming growth factors; GLP-1; GAG; cytokines; insulin-like growth factors; bone- and cartilage-inducing factors; neurotrophic factors; interleukins including IL-1, L-2, IL-3, IL-4, IL-5, IL-6, IL-7, IL-8, IL-9, IL-10, IL-11, IL-12; interferons including interferon gamma, interferon-1a, interferon alphas; TNF alpha; TNF beta; TGF-beta; cholera toxin A and B fragments; *E. coli* enterotoxin A and B fragments; secretin; enzymes including histone deacetylase, superoxide dismutase, catalase, adenosine deaminase, thymidine kinase, cytosine deaminase, proteases, lipases, carbohydrases, nucleotidases, polymerases, kinases and phosphatases; transport or binding proteins especially those which bind and/or transport a vitamin, metal ion, amino acid or lipid or lipoprotein such as cholesterol ester transfer protein, phospholipid transfer protein, HDL binding protein; connective tissue proteins such as a collagen, elastin or fibronectin; a muscle protein such as actin, myosin, dystrophin, or mini-dystrophin; a neuronal, liver, cardiac, or adipocyte protein; a cytotoxic protein; a cytochrome; a protein which is able to cause replication, growth or differentiation of cells; a signalling molecule such as an intra-cellular signalling protein or an extracellular signalling protein (eg hormone); trophic factors such as BDNF, CNTF, NGF, IGF, GMF, aFGF, bFGF, VEGF, NT3, T3 and HARP; apolipoproteins; antibody molecules; receptors in soluble form such as T-cell receptors and receptors for cytokines, interferons or chemokines; proteins or peptides containing antigenic epitopes and fragments; and derivatives, conjugates and sequence variants of any of the above. These and other proteins may be derived from human, plant, animal, bacterial or fungal sources, and extracted either from natural sources, prepared as recombinants by fermentation or chemically synthesised.

2. Polynucleotides such as long-chain linear or circular single-, double- or triple-stranded DNA, single-, double- or triple-stranded RNA, oligonucleotides such as antisense DNA or RNA, and analogues thereof including PNA and phosphothioate derivates. In one embodiment it is preferred that the polynucleotides used in the invention contain a CpG motif. The coding sequence of the polynucleotide may encode a therapeutic product, in particular the coding sequence may encode an extracellular protein (e.g. a secreted protein); an intracellular protein (e.g. cytosolic, nuclear or membrane protein); a protein present in the cell membrane; a blood protein, such as a clotting protein (e.g. kinogen, prothrombin, fibrinogen factor VII, factor VIII or factor IX), an enzyme, such as a catabolic, anabolic gastro-intestinal, metabolic (e.g. glycolysis or Krebs cycle), or a cell signalling enzyme, an enzyme which breaks down or modifies lipids, fatty acids, glycogen, amino acids, proteins, nucleotides, polynucleotides (e.g. DNA or RNA) or carbohydrate (e.g. protease, lipase or carbohydrase), or a protein modifying enzyme, such as an enzyme that adds or takes chemical moieties from a protein (e.g. a kinase or phosphatase); a transport or binding protein (e.g. which binds and/or transports a vitamin, metal ion, amino acid or lipid, such as cholesterol ester transfer protein, phospholipid transfer protein or an HDL binding protein); a connective tissue protein (e.g. a collagen, elastin or fibronectin); a muscle protein (e.g. actin, myosin, dystrophin or mini-dystrophin); a neuronal, liver, cardiac or adipocyte protein; a cytotoxic protein; a cytochrome; a protein which is able to cause the replication, growth or differentiation of cells; a protein which aids transcription or translation of a gene or regulates transcription or translation (e.g. a transcription factor or a protein that binds a transcription factor or polymerase); a signalling molecule, such as an intracellular or extracellular signalling molecule (e.g. a hormone); an immune system protein such as an antibody, T cell receptor, MHC molecule, cytokine (e.g. IL-1, IL-2, IL-3, IL-4, IL-5, IL-6, IL-7, IL-8, IL-9, IL-10, TNF-, TNF-, TGF-), an interferon (e.g. IFN-, IFN-, IFN-), chemokine (e.g. MIP-1, MIP-1, RANTES), an immune receptor (e.g. a receptor for a cytokine, interferon or chemokine, such as a receptor for any of the above-mentioned cytokines, interferons or chemokines) or a cell surface marker (e.g. macrophage, T cell, B cell, NK cell or dendritic cell surfacemarker)(e.g. CD 1, 2, 3, 4, 5, 6, 7, 8, 16, 18, 19, 28, 40, or 45; or a natural ligand thereof), a trophic factor (e.g. BDNF, CNTF, NGF, IGF, GMF, aFGF, bFGF, VEGF, NT3, T5, HARP) or an apolipoprotein; a tumour suppressor (e.g. p53, Rb, Rap1A, DCC or k-rev); a suicide protein (thymidine kinase or cytosine deaminase); or a gene repressor. The proteins and peptides encoded by the polynucleotides useful in the invention may be immunogenic i.e. contain an antigen specific to the activity of the protein against which antibodies are generated by the immune system.

The polynucleotide may have control sequences operably linked to the coding sequence. The control sequences may typically be those of any eukaryote or of a virus which infects such eukaryotes. The polynucleotide may comprise an origin of replication.

The polynucleotides may be chemically modified. This may enhance their resistance to nucleases or may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

The polynucleotide suitable for use in the invention is preferably in a form in which it is substantially free of or associated with cells or with cellular, prokaryotic, eukaryotic, nuclear, chromatin, histone Or protein material. It may be in substantially isolated form, or it may be in substantially purified form, in which case it will generally comprise more than 90%, e.g. (more than or at least) 95%, 98% or 99% of the polynucleotide or dry mass in the preparation. Thus the polynucleotide may be in the form of 'naked DNA'.

3. Polysaccharides such as heparin, low-molecular weight heparin, polymannose, cyclodextrins and lipopolysaccharide.

4. Any or all of the above either separately or in combination with each other (for example in the form of a heteroconjugate), or with additional agents.

In preferred embodiments of the invention, the active macromolecular principle to be absorbed is selected from calcitonins, insulin, low molecular weight heparin, erythropoeitin, human growth hormone and parathyroid hormone.

More preferably, the macromolecular principle is insulin, calcitonin or parathyroid hormone. When the macromolecular principle is insulin, the composition suitably further comprises an insulin sensitising agent. Insulin sensitisers are capable of increasing the body's response to the insulin absorbed. Suitable sensitisers are known in the art and examples include troglitazone, pioglitazone, rosiglitazone and other members of the glitazone class of molecules.

The non-conjugated bile acid or salt is suitably chosen from chenodeoxycholic acid, deoxycholic acid, cholic acid or the sodium salts thereof. The bile salt is preferably chenodeoxycholate.

The additive is chosen from propyl gallate and butyl hydroxy anisole and analogues and derivatives thereof, and an organic acid or a pharmaceutically acceptable salt thereof, or mixtures thereof, which additive is capable of allowing the non-conjugated bile salt to remain in solution when added to intestinal fluids at pH levels between 5 and 6.5, and which, when introduced into the intestine does not raise the pH of the intestinal fluid above pH 7.5.

The additive may be propyl gallate or a derivative thereof. Suitable derivatives of propyl gallate include esters of gallic acid. The esters may be linear or branched chain $C_{1-12}$ alkyl, $C_{1-12}$ alkyloxy, $C_{1-12}$ alkylthio or $C_{2-12}$ alkenyl esters. The compounds are optionally substituted with halogen, linear or branched chain $C_{1-12}$ alkyl, $C_{1-12}$ alkyloxy, $C_{1-12}$ alkylthio or $C_{2-12}$ alkenyl esters.

The additive may also be BHA or an analogue or derivative thereof. Suitable analogues or derivatives thereof include analogues and derivatives of hydroxy anisole where the methyl group or the methoxy group linked to the aromatic ring and/or the hydrogen ortho to the hydroxyl group are replaced by linear or branched chain $C_{1-12}$ alkyl, $C_{1-12}$ alkyloxy, $C_{1-12}$ alkylthio or $C_{2-12}$ alkenyl, either unsubstituted or substituted in any position, especially by halogen atoms.

The ratio of bile salt to additive, e.g. propyl gallate, is preferably from 1:1 to 5:1, more preferably from 4:3 to 5:2, and most preferably about 2:1 by weight.

The additive is preferably propyl gallate, and suitably the ratio of bile salt to propyl gallate is most preferably about 2:1 by weight.

In a preferred embodiment of the invention, the non-conjugated bile salt is chenodeoxycholate and the additive is propyl gallate.

The amount of non-conjugated bile salt/additive (absorption enhancer) and active macromolecular principle in the composition of the invention is chosen so as to achieve, at the intestinal cell barrier layer (intestinal wall), an effective concentration of non-conjugated bile salt/additive absorption enhancer so as to cause enhanced absorption in the co-presence of a suitable amount of the active macromolecular principle which, when absorbed, will exert its normal beneficial effect. The practitioner of the invention would select the amounts of the non-conjugated bile salt/additive absorption enhancer and active macromolecular principle on the basis of the amount (for example, blood concentration level) of the active macromolecular principle concerned which is necessary for therapeutic effectivity. For example, the weight ratio of the total weight of the non-conjugated bile salt/additive absorption enhancer to the active macromolecular principle in the mixture contained in the capsule may preferably be from 1:1 to 200:1, more preferably from 3:1 to 100:1, and most preferably from 5:1 to 50:1.

The absolute amount of the active macromolecular principle would be selected on the basis of the dosage of the substance required to exert the normal beneficial effect with respect to the dosage regimen used and the patient concerned. Determination of these dosage amounts falls within the mantle of the practitioner of the invention.

The composition of the invention may further comprise one or more other absorption enhancer compounds, for example, medium chain monoglycerides, chelating agents etc.

The composition of the invention may optionally further comprise any conventional additive used in the formulation of pharmaceutical products including, for example, anti-oxidants, anti-microbials, suspending agents, fillers, diluents, absorbents, glidants, binders, anti-caking agents, lubricants, disintegrants, swelling agents, viscosity regulators, plasticisers and acidity regulators (particularly those adjusting the intestinal milieu to between 7 and 7.5). Suitable swelling agents include sodium starch glycolate, pregelatinised starch, microcrystalline cellulose, crosprovidone and magnesium aluminium silicate or mixtures thereof. Sodium starch glycolate and other polysaccharide-based swelling agents may be present in an amount of from 5 to 10% by weight. Crosprovidone may be present in an amount of from 5 to 30% by weight.

In the composition of the invention where the mixture is contained in a capsule or tablet, the formulation is preferably substantially anhydrous. In more preferred embodiments of the invention the entire composition is substantially anhydrous. Substantially anhydrous in the context of this invention means less than 5%, preferably less than 1% and more preferably less than 0.5% water by weight of the mixture.

The composition of the invention can, depending on the active macromolecular principle used therein, be used in the treatment of a variety of conditions and diseases of the human or animal body by therapy or, alternately, can be used to introduce macromolecules essential for the diagnosis of diseases and conditions within the human or animal body. The compositions of the invention are preferably pharmaceutical or cosmetic compositions.

In the composition of the invention, the mixture contained in the capsule may be a liquid, semi-solid or gel, which is either in the form of a solution or a microparticulate dispersion. That is to say the active macromolecular principle(s) for absorption are incorporated into the formulation either in the form of a solution or as a microparticulate dispersion. Alternatively, the composition may be in the form of a solid.

The compositions of the invention are suitably produced by preparing a substantially anhydrous mixture of the active macromolecular principle and the bile salt/additive absorption enhancer and then filling uncoated capsules with the mixture and then coating them with an appropriate polymer mixture to achieve the desired permeability properties. Depending on the nature of additional excipients employed, the pharmaceutical composition of the invention may be in liquid, solid, semi-solid or gel form. The pharmaceutical composition of the invention is suitable for administration via any route giving access to different mucosal tissues such as buccal and sublingual mucosa, the nasal palate, the lungs, the rectum, the intestinal tract (including the large and small intestines) and the vagina. In the case of liquid, semi-solid or gel formulations, these may be either anhydrous or aqueous.

Where the intended site of action of the composition of the invention is the intestine, it is desirable that the composition is enclosed within an enteric coating which can withstand the stomach, so that the components of the formulation remain together, undiluted and in close association until they reach the tissues of the small intestine or colon. Such formulations will suitably be anhydrous. Compositions in liquid form will suitably be administered as enteric-coated capsules, while solid formulations may be administered either within enteric-coated capsules, or in tablet form, preferably enteric-coated tablets.

The enteric coating is chosen appropriately to withstand the natural condition of the stomach and to become permeable at the desired location in the intestine. This is preferably determined by the pH conditions that modulate along the length of the intestine. Where the site of action is the small intestine, it is preferred that the enteric coating becomes permeable and releases its contents at a pH of from 3 to 7, preferably from 5.5 to 7, more preferably from 5.5 to 6.5. Where the intended site of action is the colon, it is preferred that the enteric coating becomes permeable and releases its contents at a pH of 6.8 or above.

Suitable enteric coatings are well known in the art and include cellulose acetate, phthalate, shellac and polymethacrylates such as those selected from the L and S series of Eudragits in particular Eudragits L12.5P, L12.5, L100, L100-55, L30 D-55, S12.5P, S12.5 and S100. Suitable plasticisers or wetting agents, such as triethyl citrate and polysorbate 80 may also be included in the coating mixture.

Selection of an appropriate coating for the capsule, which is preferably an HPMC or a gelatine capsule, can readily be made by the person skilled in the art based on their knowledge and the available literature supporting the Eudragit products.

Where the intended site of action is the nasal mucosa, the formulation may be in the form of an aqueous solution or as a dry powder, which can be administered as a spray.

Where the intended site of action is the rectum, an appropriate method of administration is as an anhydrous liquid or solid enclosed within a capsular shell, or incorporated into the matrix of an erodible suppository.

For vaginal application, adminstration of the formulation in gel form is also appropriate.

The following Examples serve to illustrate the present invention and should not be construed as limiting.

EXAMPLES

Example 1

Preparation of Chenodeoxycholate/Propyl Gallate Mixture Containing Insulin as Active Macromolecular Principle 1 g of chenodeoxycholic acid is dissolved in 3.4 g of sodium hydroxide solution (30 mg/ml) with warming. The solution is brought to room temperature and adjusted to pH 7.85 by addition of further sodium hydroxide solution. 500 mg of propyl gallate is then added and dissolved by shaking at room temperature. The pH is adjusted to 7.45, and 56.25 mg of recombinant human insulin is added with stirring at 37° C. After all the solid has dissolved, the solution is made up to a total weight of 8 g with distilled water, frozen and lyophilised overnight to give a dry crystalline powder.

A formulation containing chenodeoxycholate alone is prepared in an identical manner to that described above, except that propyl gallate is omitted where appropriate. As before, the pH of the final solution before drying is adjusted to lie between 7.4 and 7.5.

Example 2

Preparation of Chenodeoxycholate/Butylated Hydroxy Anisole Mixture

An identical method to that described in Example 3 is employed, except that butylated hydroxy anisole is used instead of propyl gallate.

Example 3

Dissolution of Chenodeoxycholate, with or without Propyl Galate, in Simulated Intestinal Fluid Simulated intestinal fluids are prepared according to the recipes given below, where '-', 'L' and 'H' refers to different concentrations of salt in the fluids—zero, low and high respectively.

| Low pH (fed state) buffer | | | | |
|---|---|---|---|---|
| Component | pH 5.0/— | pH 5.0/L | pH 5.0/H | |
| Acetic acid | 8.65 g | 8.65 g | 8.65 g | |
| Sodium taurocholate | 8.12 g | 8.12 g | 8.12 g | 15 mM |
| Lecithin | 2.8 g | 2.8 g | 2.8 g | 3.75 mM |
| Potassium Chloride | — | 7.7 g | 15.2 g | |
| Distilled water | 1 litre | 1 litre | 1 litre | |
| Sodium hydroxide | to pH 5 | to pH 5 | to pH 5 | |

| Low pH (fasted state) buffer | | | | |
|---|---|---|---|---|
| Component | pH 6.5/— | pH 6.5/L | pH 6.5/H | |
| Potassium dihydrogen phosphate | 3.9 g | 3.9 g | 3.9 g | |
| Sodium taurocholate | 1.6 g | 1.6 g | 1.6 g | 3 mM |
| Lecithin | 0.6 g | 0.6 g | 0.6 g | 0.75 mM |
| Potassium Chloride | — | 7.7 g | 15.2 g | |
| Distilled water | 1 litre | 1 litre | 1 litre | |
| Sodium hydroxide | to pH 6.5 | to pH 6.5 | to pH 6.5 | |

Figure 1A:
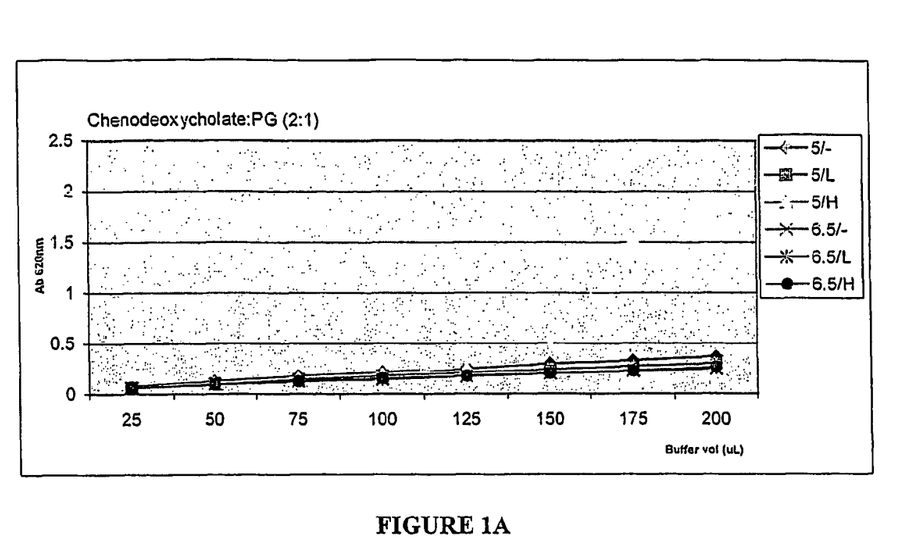
FIGS. 1A and 1B show the solubility of a chenodeoxycholate/propyl gallate mixture (FIG. 1A) and chenodeoxycholate alone (FIG. 1B) in a simulated intestinal fluid.
Figure 1B:
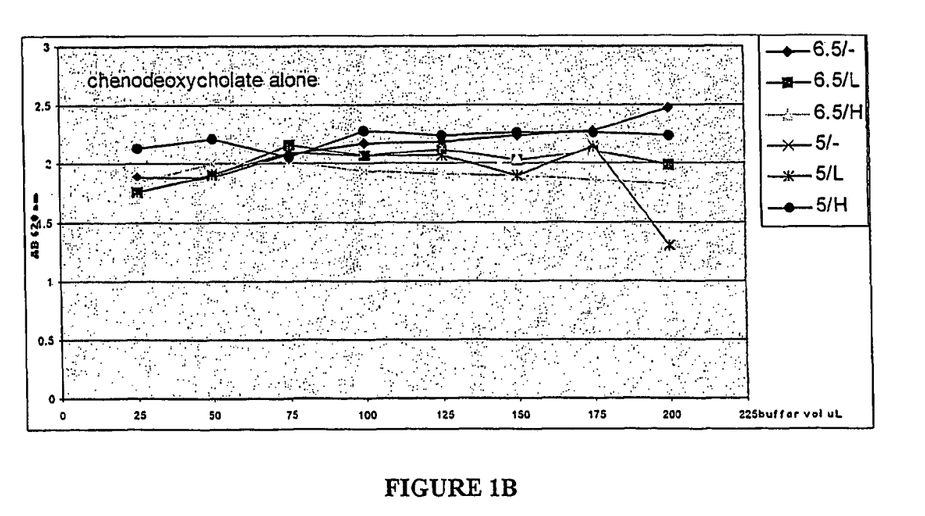
Figure 2:
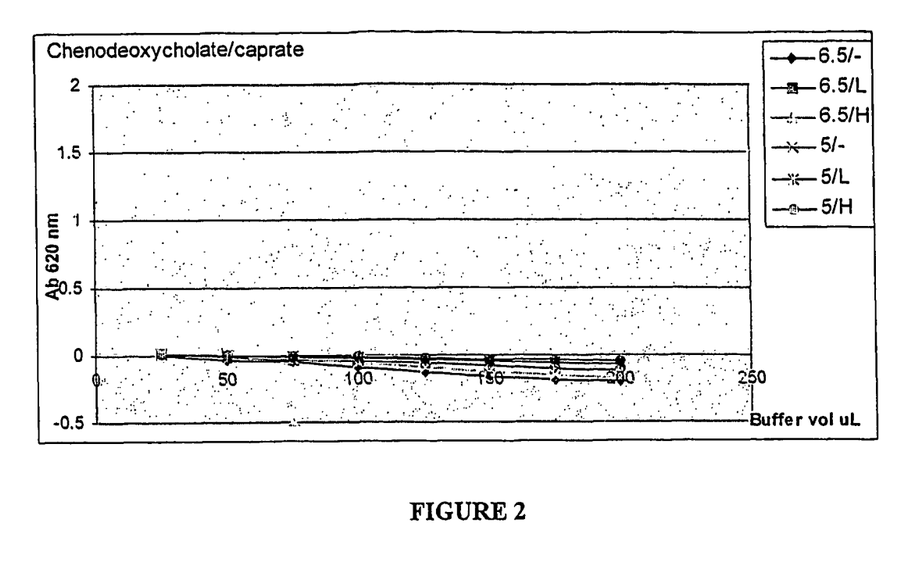
FIG. 2 shows the solubility of a chenodeoxycholate/caproate mixture in a simulated intestinal fluid.

6×10 mg of dry powders as prepared in example 1 are placed in separate wells of a flat-bottomed 96-well microtitre plate, and successive aliquots of 25 µl of SIF are added at 15 minute intervals with incubation at 37° C. Solubility is assessed after gentle mixing by determining the optical clarity of the well contents in a plate reader at 620 nm. Increasing optical density (>0.5) in the graphs of FIGS. 1A and 1B indicates the presence of precipitates. As can be seen, when 10 mg chenodeoxycholate is diluted out to 150 µl volume, precipitation occurs under all conditions tested, in contrast to the chenodeoxycholate/propyl gallate mixture, which remains dissolved in all variants of simulated intestinal fluid tested.

Example 4

Dissolution of Chenodeoxycholate/Butylated Hydroxy Anisole Mixture in Simulated Intestinal Fluid Identical conditions to those employed in Example 3 are used, except that a chenodeoxycholate/butylated hydroxy anisole mixture as prepared in Example 2 is employed. Essentially clear solutions are obtained upon dilution of 10 mg in up to 200 µl of all intestinal fluid buffers described.

Example 5

Figure 3:
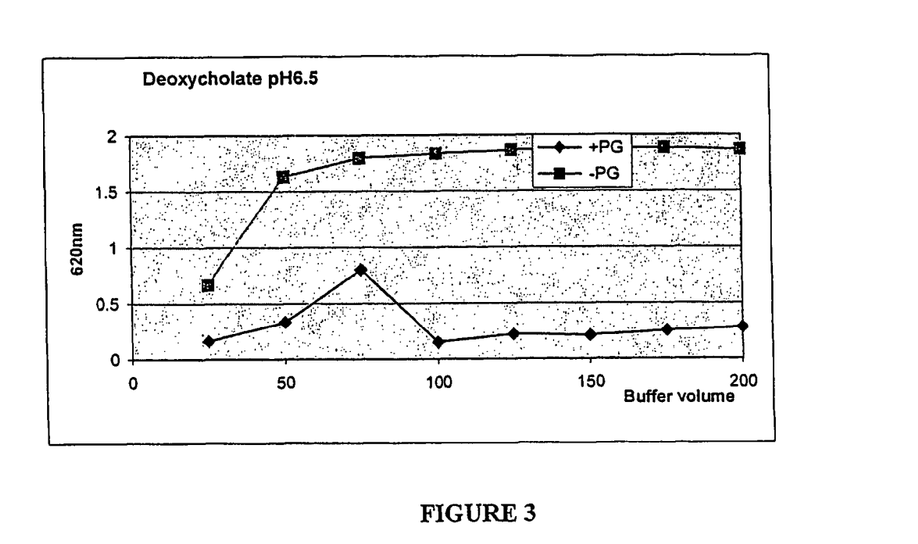
FIG. 3 shows the solubility of a deoxycholate/propyl gallate mixture in a simulated intestinal fluid.
Figure 4:
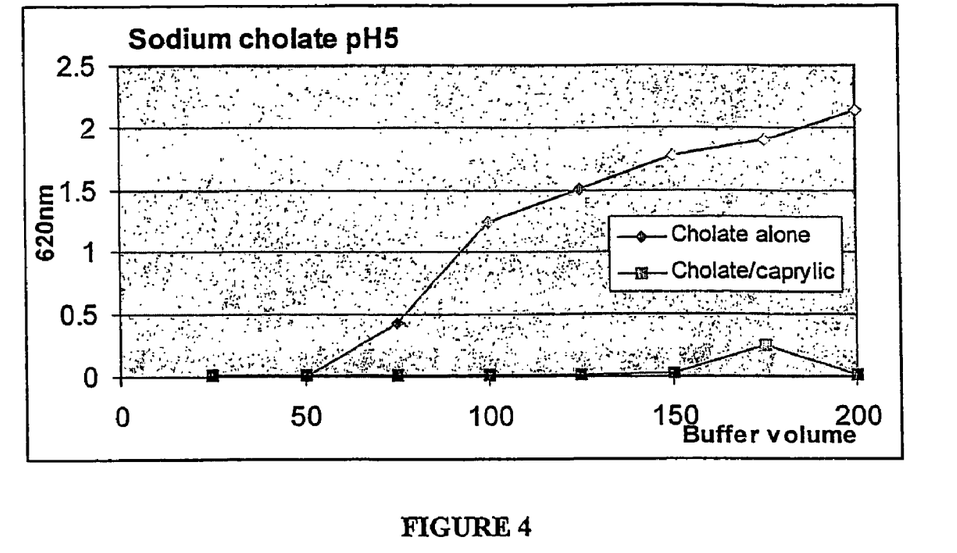
FIG. 4 shows the solubility of a cholate/sodium caproate mixture in a simulated intestinal fluid.

Dissolution of Deoxycholate/Propyl Gallate Mixture in Simulated Intestinal Fluid Identical conditions to those employed in Example 3 are used, except that deoxycholic acid is employed instead of chenodeoxycholic acid, and the ratio of bile salt to propyl gallate is 1:1 wt:wt. Essentially clear solutions are obtained upon dilution of 10 mg in up to 200 µl of intestinal fluid buffer at pH 6.5, in contrast to formulations where sodium deoxycholate alone is employed. The results are shown in FIG. 3.

Example 6

In Vivo Efficacy of Chenodeoxycholate/Propyl Gallate/Insulin Mixture in Juvenile Pigs Formulations as prepared in example 1 (containing 100 iu insulin, 66 mg chenodeoxycholic acid and 33 mg propyl gallate or 100 iu insulin and chenodeoxycholic acid alone) are administered as dry compacted powders via a stoma into the jejunum of eight juvenile pigs (each ~40 kg weight). Blood glucose levels are measured at intervals over a six hour period and mean change in AUC of plasma glucose is calculated in h·mmol/l. As can be seen from the summary of data below, inclusion of PG in the formulation gives a higher degree of reproducibility, and a higher degree of efficacy.

|  | Number of responders | AUC |
|---|---|---|
| Insulin/Cheno/PG | 8/8 | −3.23 |
| Insulin/Cheno alone | 4/8 | −1.40 |

Example 7

In Vivo Efficacy of Tablets Containing Chenodeoxycholate/Propyl Gallate/Calcitonin Mixture in Juvenile Pigs Formulations as prepared in Example 1 (containing 1 mg salmon calcitonin (sCT, 5000 iu), 66 mg chenodeoxycholic acid, 33 mg propyl gallate, 1 mg fumed silica and 20 mg crospovidone) are administered as compacted tablets via a stoma into the jejunum of eight juvenile pigs (each ~40 kg weight). Blood calcium levels are measured at intervals over a six hour period and mean change in AUC of plasma calculated is calculated in h·mmol/l. As can be seen from the summary of data below, the formulation gives a significant sCT-related lowering in calcium, compared with the control.

| Treatment | AUC | Standard deviation |
|---|---|---|
| Sham administration | −0.03 | 0.23 |
| 400 iu salmon calcitonin s.c. | −1.79 | 1.18 |
| Formulation i.j. | −2.35 | 1.03 |

Example 8

In Vivo Efficacy of Capsules Containing Chenodeoxycholate/Propyl Gallate/Insulin Mixture in Juvenile Pigs Formulations as prepared in Example 1 (containing 100 iu insulin, 66 mg chenodeoxycholic acid, 33 mg propyl gallate, 1 mg fumed silica, 22 mg crospovidone and 13 mg of magnesium aluminium silicate) are administered as a dry powder inside a hydroxypropyl methyl cellulose capsule via a stoma into the jejunum of four juvenile pigs (each ~40 kg weight). A control group is run, receiving PBS alone via the stoma. Blood glucose levels are measured at intervals over a six hour period and mean change in AUC of plasma glucose is calculated in h·mmol/l, shown in the Table below.

| Treatment | Responders | AUC |
|---|---|---|
| Sham administration | 4/4 | −4.2 |
| Formulation i.j. | 0/4 | −1.4 |

Example 9

In Vivo Efficacy of Chenodeoxycholate/Propyl Gallate/Insulin Mixture in Healthy Human Volunteers A formulation is prepared in Example 1, containing active and excipients in the following proportions:

| Insulin | 87 iu |
|---|---|
| Propyl gallate | 33 mg |
| Chenodeoxycholate | 66 mg |
| Fumed silica | 1 mg |
| Sodium starch glycolate | 0.5 mg |

Quantities of the formulation containing 170 iu and 340 iu are dissolved in 2 ml and 4 ml of distilled water respectively and administered to healthy volunteers via a naso-jejunal cannula. Insulin levels are seen to rise within ten minutes of administration, and peak values obtained for treated and control groups are shown in the Table below.

| Treatment | Mean value (pmol/litre) | s.d. |
|---|---|---|
| Control (all subjects, no treatment) | 6.0 | 1.7 |
| 170 iu (3 subjects) | 25.0 | 3.6 |
| 340 iu (2 subjects) | 553.5 | 283.5 |

The invention claimed is:
1. A solid pharmaceutical composition comprising a mixture of:
 (a) an active macromolecular principle which is a polypeptide or protein, polynucleotide or polysaccharide;
 (b) a non-conjugated bile acid or salt; and
 (c) an additive chosen from
  (i) propyl gallate or a linear or branched chain $C_{1-12}$ alkyl, $C_{1-12}$ alkyloxy, $C_{1-12}$ alkylthio or $C_{2-12}$ alkenyl ester of gallic acid which is optionally substituted with one or more groups which are the same or dif- ferent and are selected from halogen and linear or branched chain $C_{1-12}$ alkyl, $C_{1-12}$ alkyloxy, $C_{1-12}$ alkylthio or $C_{2-12}$ alkenyl;
(ii) butyl hydroxy anisole, or hydroxy anisole wherein the methoxy group linked to the aromatic ring and/or the hydrogen ortho to the hydroxyl group is/are replaced by one or more groups which are the same or different and are selected from linear or branched chain $C_{1-12}$ alkyl, $C_{1-12}$ alkyloxy, $C_{1-12}$ alkylthio and $C_{2-12}$ alkenyl, either unsubstituted or substituted in any position by one or more halogen atoms; and
(iii) a mixture of (i) and (ii)

wherein the mixture comprises at least 1% by weight of the additive (c), wherein the ratio by weight of the non-conjugated bile salt+additive (b+c) to the active macromolecular principle is at least 3:1 and wherein the composition, when introduced into the intestine, does not raise the pH of the intestinal fluid above pH 7.0.

2. A composition according to claim 1, which comprises less than 5% by weight of water.

3. A composition according to claim 1, wherein the ratio by weight of the non-conjugated bile salt+additive (b+c) to the active macromolecular principle is at least 5:1.

4. A composition according to claim 1, wherein the mixture is in the form of a solution or a microparticulate dispersion.

5. A composition according to claim 1, wherein the mixture is in solid form.

6. A composition according to claim 1, where the active macromolecular principle is chosen from insulin, calcitonin, growth hormone, parathyroid hormone, erythropoietin, GLP1 and GCSF, or is single, double or triple-stranded RNA.

7. A composition according to claim 6, where the active macromolecular principle is insulin, calcitonin or parathyroid hormone.

8. A composition according to claim 7, where the active macromolecular principle is insulin and the composition further comprises an insulin sensitizing agent.

9. A composition according to claim 1, wherein component (b) is chenodeoxycholate.

10. A composition according to claim 1, wherein the additive is propyl gallate or a linear or branched chain $C_{1-12}$ alkyl, $C_{1-12}$ alkyloxy, $C_{1-12}$ alkylthio or $C_{2-12}$ alkenyl ester of gallic acid which is optionally substituted with one or more groups which are the same or different and are selected from halogen and linear or branched chain $C_{1-12}$ alkyl, $C_{1-12}$ alkyloxy, $C_{1-12}$ alkylthio or $C_{2-12}$ alkenyl.

11. A composition according to claim 1, wherein the additive is butyl hydroxy anisole or hydroxy anisole where the methoxy group linked to the aromatic ring and/or the hydrogen ortho to the hydroxyl group are replaced by linear or branched chain $C_{1-12}$ alkyl, $C_{1-12}$ alkyloxy, $C_{1-12}$ alkylthio or $C_{2-12}$ alkenyl, either unsubstituted or substituted in any position by one or more halogen atoms.

12. A composition according to claim 1, wherein the composition is coated with an enteric coating which becomes permeable at a pH from 3 to 7.

13. A pharmaceutical composition according to claim 12, wherein the enteric coating becomes permeable at a pH from 5.5 to 7.

14. A pharmaceutical composition according to claim 13, wherein the enteric coating becomes permeable at a pH from 5.5 to 6.5.

15. A composition according to claim 1, wherein the composition, when introduced into the intestine, enhances absorption of the active macromolecular principle due to the additive improving solubility of the bile salt.

16. A composition according to claim 1, which is water soluble.

17. A composition according to claim 1, which is an oral pharmaceutical composition, and wherein, when the composition is introduced into the intestines, the additive (c) enhances the solubility of the non-conjugated bile salt.

18. A composition according to claim 1, wherein the additive allows the non-conjugated bile acid or salt to remain in solution when added to intestinal fluids at pH levels between 5 and 6.5.

19. A composition according to claim 1, which does not comprise an agent which, when introduced into the intestine, raises the pH of the intestinal fluid above pH 7.5.

20. A method of enhancing the absorption of an active macromolecular principle in a patient, which method comprises administering to said patient a composition as defined in claim 1.

21. A method of enhancing the absorption of an active macromolecular principle which is polypeptide or protein, polynucleotide or polysaccharide across the intestinal wall in a human or animal body, which method comprises administering a non-conjugated bile acid or salt, together with an additive chosen from:
(i) propyl gallate or a linear or branched chain $C_{1-12}$ alkyl, $C_{1-12}$ alkyloxy, $C_{1-12}$ alkylthio or $C_{2-12}$ alkenyl ester of gallic acid which is optionally substituted with one or more groups which are the same or different and are selected from halogen and linear or branched chain $C_{1-12}$ alkyl, $C_{1-12}$ alkyloxy, $C_{1-12}$ alkylthio or $C_{2-12}$ alkenyl;
(ii) butyl hydroxy anisole, or hydroxy anisole wherein the methoxy group linked to the aromatic ring and/or the hydrogen ortho to the hydroxyl group is/are replaced by one or more groups which are the same or different and are selected from linear or branched chain $C_{1-12}$ alkyl, $C_{1-12}$ alkyloxy, $C_{1-12}$ alkylthio and $C_{2-12}$ alkenyl, either unsubstituted or substituted in any position by one or more halogen atoms; and
(iii) a mixture of (i) and (ii)

together with the active macromolecular principle in a solid pharmaceutical composition, wherein the additive accounts for at least 1% by weight of the total weight of (a) the active macromolecular principle, (b) the non-conjugated bile acid or salt, plus (c) the additive, wherein the ratio by weight of the non-conjugated bile salt+additive (b+c) to the active macromolecular principle is at least 3:1 and wherein the composition, when introduced into the intestine, does not raise the pH of the intestinal fluid above pH 7.0, which method enhances the absorption of the active macromolecular principle due to the additive improving the solubility of the bile salt.

22. A method according to claim 21 wherein the active macromolecular principle to be absorbed is chosen from insulin, calcitonin, growth hormone, parathyroid hormone, erythropoietin, GLP1 and GCSF, or is single, double or triple-stranded RNA.

23. A method according to claim 22, wherein the active macromolecular principle to be absorbed is insulin, calcitonin or parathyroid hormone.

24. A method according to claim 23, wherein the active macromolecular principle to be absorbed is insulin and an insulin sensitizing agent is also present.

25. A method according to claim 21, wherein the composition comprises less than 5% by weight of water.

26. A method according to claim 21, wherein the active macromolecular principle, which is a polypeptide or protein, polynucleotide or polysaccharide, the non-conjugated bile acid or salt and the additive are formulated as a solution, a microparticulate dispersion or a solid.

27. A method according to claim 21, wherein the composition is coated with an enteric coating which becomes permeable at a pH from 3 to 7.

28. A method according to claim 27, wherein the enteric coating becomes permeable at a pH from 5.5 to 7.

29. A method according to claim 28, wherein the enteric coating becomes permeable at a pH from 5.5 to 6.5.

30. A method according to claim 21, wherein the composition is water soluble.

31. A method according to claim 21, wherein the additive allows the non-conjugated bile acid or salt to remain in solution when added to intestinal fluids at pH levels between 5 and 6.5.

32. A method according to claim 21, wherein the composition does not comprise an agent which, when introduced into the intestine, raises the pH of the intestinal fluid above pH 7.5.

* * * * *